United States Patent [19]

Cassidy

[11] Patent Number: 4,631,282
[45] Date of Patent: Dec. 23, 1986

[54] ANTIHYPERTENSIVE CHROMANS AND CHROMENES

[75] Inventor: Frederick Cassidy, Harlow, England

[73] Assignee: Beecham Group Plc, England

[21] Appl. No.: 746,968

[22] Filed: Jun. 20, 1985

[30] Foreign Application Priority Data

Jun. 22, 1984 [GB] United Kingdom ............... 8415931
Dec. 13, 1984 [GB] United Kingdom ............... 8431479

[51] Int. Cl.[4] ............... A61K 31/495; C07D 405/04
[52] U.S. Cl. .................... 514/254; 514/278;
514/320; 514/389; 514/409; 514/422; 544/230;
544/376; 546/15; 546/196; 548/309; 548/407;
548/525
[58] Field of Search ............... 546/15, 196; 544/230,
544/376; 548/309, 407, 525; 514/409, 422, 278,
320, 389, 254

[56] References Cited
U.S. PATENT DOCUMENTS 4,248,882 2/1981 Sarges .................... 548/309 X
4,510,152 4/1985 Farvic .................... 546/196 X
4,542,149 9/1985 Evans et al. ............. 546/196 X Primary Examiner—Richard A. Schwartz
Attorney, Agent, or Firm—Jacobs & Jacobs

[57] ABSTRACT

Antihypertensive compounds of formula (I):

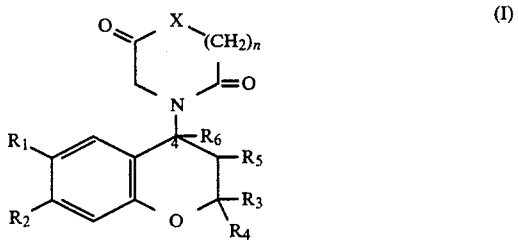

wherein the various substituents are defined hereinbelow.

12 Claims, No Drawings

ANTIHYPERTENSIVE CHROMANS AND CHROMENES

The present invention relates to novel chromans and chromenes having pharmacological activity, to a process for preparing them, to pharmaceutical compositions containing them, and to their use in the treatment of mammals.

U.S. Pat. Nos. 4,110,347 and 4,119,643 and 4,251,532 and European Patent Publications Nos. 28 064 and 28 449 disclose classes of compounds that are described as having blood pressure lowering activity or anti-hypertensive activity.

European Patent Publications No. 76 075, 91 748, 93 534 and 95 310 disclose classes of chromans that are described as having blood pressure lowering activity. In addition, European Patent Publication No. 93 535 discloses a class of chromans and chromenes that are also described as having blood pressure lowering activity.

A further class of chromans and chromenes has now been discovered which contain a lactam ring that substitutes the chroman or chromene in the 4-position, the lactam ring having a second carbonyl group. In addition, such chromans and chromenes have been found to have blood pressure lowering activity. It is also believed that these compounds have a mechanism of action which indicates that they are of potential use in the treatment of other cardiovascular disorders such as congestive heart failure, angina, peripheral vascular disease and cerebral vascular disease; and disorders associated with smooth muscle contraction of the gastro-intestinal tract (such as peptic ulcers, irritable bowel syndrome and diverticular disease), respiratory system (such as reversible airways obstruction and asthma) and uterus (such as premature labour).

Accordingly, the present invention provides a compound of formula (I):

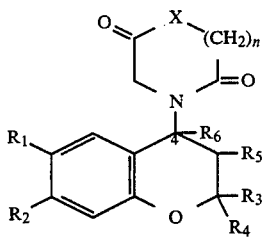

(I)

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;

one of $R_3$ and $R_4$ is hydrogen or $C_{1-4}$ alkyl and the other is $C_{1-4}$ alkyl or $R_3$ and $R_4$ together are $C_{2-5}$ polymethylene;

either $R_5$ is hydrogen, hydroxy, $C_{1-6}$ alkoxy or $C_{1-7}$ acyloxy and $R_6$ is hydrogen or $R_5$ and $R_6$ together are a bond;

n is 0 or 1; and

X is $CH_2$ or $NR_7$ wherein $R_7$ is hydrogen or $C_{1-6}$ alkyl;

the nitrogen-containing group in the 4-position being trans to the $R_5$ group when $R_5$ is hydroxy, $C_{1-6}$ alkoxy or $C_{1-7}$ acyloxy; or a pharmaceutically acceptable salt or solvate thereof.

When one of $R_1$ and $R_2$ is hydrogen, the other is preferably selected from the class of $C_{1-6}$ alkylcarbonyl, $C_{1-6}$ alkoxycarbonyl, nitro or cyano. In particular, when one of $R_1$ and $R_2$ is hydrogen, the other is preferably acetyl, nitro or cyano, especially nitro or cyano.

When one of $R_1$ and $R_2$ is hydrogen, it is preferred that $R_2$ is hydrogen.

When one of $R_1$ and $R_2$ is nitro, cyano or $C_{1-3}$ alkylcarbonyl, the other is preferably amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano, especially cyano, and the other is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alkyl-containing groups for $R_1$ and $R_2$ are, preferably, methyl or ethyl.

Preferably, $R_3$ and $R_4$ are both $C_{1-4}$ alkyl. In particular, they are both methyl or ethyl, preferably both methyl.

When $R_5$ is $C_{1-6}$ alkoxy and $R_6$ is hydrogen, preferred examples of $R_5$ include methoxy and ethoxy, of which methoxy is more preferred. When $R_5$ is $C_{1-7}$ acyloxy and $R_6$ is hydrogen, a preferred class of $R_5$ is unsubstituted carboxylic acyloxy, such as unsubstituted aliphatic acyloxy or benzoyloxy. However, it is more preferred that $R_5$ and $R_6$ together are a bond or that $R_5$ and $R_6$ are both hydrogen, or, in particular, that $R_5$ is hydroxy and $R_6$ is hydrogen.

n is preferably 0 when X is $CH_2$ and 0 or 1 when X is $NR_7$.

When $R_7$ is $C_{1-6}$ alkyl or is a $C_{1-6}$ alkyl-containing group, the alkyl moiety is, favourably, methyl or ethyl. $R_7$ is preferably methyl.

There is a group of compounds within formula (I) wherein X is $CH_2$, n is 0 and the remaining variables are as defined under formula (I).

The compounds of formula (I) are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%. One preferred pharmaceutically acceptable form is the crystalline form, including such form in a pharmaceutical composition.

Examples of a pharmaceutically acceptable salt of a compound of formula (I) include the acid addition salts of a compound of formula (I), wherein one or the other of $R_1$ and $R_2$ is an amino or an amino-containing group, for example the hydrochloride and hydrobromide salts.

Examples of a pharmaceutically acceptable solvate of a compound of formula (I) include the hydrate.

The compounds of formula (I), wherein $R_5$ is hydrogen, hydroxy, $C_{1-6}$ alkoxy or $C_{1-7}$ acyloxy and $R_6$ is hydrogen, are asymmetric and, therefore, can exist in the form of optical isomers. The present invention extends to all such isomers individually and as mixtures, such as racemic modifications.

Examples of compounds of formula (I) include the compounds prepared in the Examples hereinafter.

The present invention also provides a process for the preparation of a compound of formula (I), which comprises the reaction of a compound of formula (II):

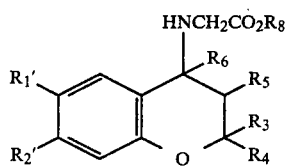

(II)

wherein $R_8$ is a protecting group; $R_1'$ is $R_1$ as hereinbefore defined or a group or atom convertible thereto, $R_2'$ is $R_2$ as hereinbefore defined or a group or atom convertible thereto, and $R_3$, $R_4$, $R_5$, and $R_6$ are as hereinbefore defined, with (i) when n is 0 and X is $NR_7$, a compound of formula (III):

(III)

wherein $R_7$ is as hereinbefore defined;

(ii) when n is 0 or 1 and X is $CH_2$, a compound of formula (IV)

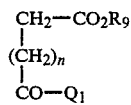

(IV)

wherein $R_9$ is a protecting group and $Q_1$ is a leaving group, followed by treatment with base;

(iii) when n is 1 and X is $NR_7$, a compound of formula (V):

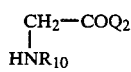

(V)

wherein $Q_2$ is a leaving group $R_{10}$ is a protecting group, followed by removal of $R_{10}$; in the case where $R_1'$ is a group or atom convertible into $R_1$, converting the group or atom into $R_1$; in the case where $R_2'$ is a group or atom convertible into $R_2$, converting the group or atom into $R_2$; optionally converting $R_1$ or $R_2$ in the resulting compound of formula (I) into another $R_1$ or $R_2$; optionally converting the resulting compound of formula (I), wherein $R_5$ is hydroxy and $R_6$ is hydrogen, into another compound of formula (I) wherein $R_5$ is $C_{1-6}$ alkoxy or $C_{1-7}$ acyloxy and $R_6$ is hydrogen, or optionally dehydrating the resulting compound of formula (I), wherein $R_5$ is hydroxy and $R_6$ is hydrogen, so as to obtain the corresponding compound of formula (I), wherein $R_5$ and $R_6$ together are a bond, and optionally reducing the resulting compound of formula (I), wherein $R_5$ and $R_6$ together are a bond, so as to obtain the corresponding compound of formula (I) wherein $R_5$ and $R_6$ are both hydrogen; and optionally forming a pharmaceutically acceptable salt or solvate.

Suitable values for $R_8$ in formula (II) include $C_{1-6}$ alkyl, such as ethyl.

The reaction (i) preferably takes place in an inert solvent such as dichloromethane at low temperatures around 5° C., followed by warming to ambient temperatures for the final cyclisation step to give the compound of formula (I).

Suitable values for $R_9$ in formula (IV) include $C_{1-6}$ alkyl such as ethyl. Suitable values for $Q_1$ include halo, such as chloro.

The reaction (ii) preferably takes place under conditions as for reaction (i). The final base catalysed cyclisation takes place preferably by sodium ethoxide in ethanol/water, at ambient temperatures 0° to 50° C.

$R_{10}$ in formula (V) is favourably a benzyloxycarbonyl group or a t-butyloxycarbonyl group, preferably a benzyloxycarbonyl group. $Q_2$ is preferably an hydroxy group.

The reaction (iii) takes place under conventional conditions for peptide coupling reactions i.e. when $Q_2$ is hydroxy, the reaction takes place in the presence of a condensation promoting agent such as dicyclohexylcarbodiimide, optionally in the presence of an acid acceptor, such as hydroxybenzotriazole.

Examples of conversions of a group or atom for $R_1'$ or $R_2'$ into $R_1$ or $R_2$ are generally known in the art of aromatic chemistry. For example, if it is desired to obtain a compound of formula (I), wherein one of $R_1$ and $R_2$ is hydrogen and the other is nitro, it is possible to carry out the reaction between the compounds of formulae (II) and (III) with one of $R_1'$ and $R_2'$ being hydrogen and the other being acetamido and then to nitrate the resulting compound in conventional manner and subsequently to convert the acetamido group into a hydrogen atom by hydrolysis, diazotisation and decomposition in conventional manner.

If the optional conversion of the resulting compound of formula (I) wherein $R_5$ is hydroxy and $R_6$ is hydrogen, into another compound of formula (I) wherein $R_5$ is $C_{1-7}$ acyloxy and $R_6$ is hydrogen, is to be carried out, then it is preferred first to protect any unsubstituted terminal amine that may be present for $R_1$ or $R_2$ and after the acylation reaction to convert the protected amino moiety into the required terminal amine. Examples of protecting groups and their addition and removal are generally known in the art.

Examples of an optional conversion of $R_1$ or $R_2$ in the resulting compound of formula (I) into another $R_1$ or $R_2$, as hereinbefore defined, include the optional conversion of an α-hydroxyethyl group into acetyl by oxidation, the optional conversion of an amino group into a chloro atom by diazotisation and reaction with a chloride salt, the optional conversion of an amino group into an amino group substituted by one or two $C_{1-6}$ alkyl or by $C_{2-7}$ alkanoyl, or the optional conversion of a hydrogen atom into a nitro group by nitration.

The optional conversion of the resulting compound of formula (I) wherein $R_5$ is hydroxy and $R_6$ is hydrogen, into another compound of formula (I) wherein $R_5$ is $C_{1-6}$ alkoxy or $C_{1-7}$ acyloxy and $R_6$ is hydrogen, may be carried out respectively by alkylation using an alkyl iodide in an inert solvent, such as toluene, in the presence of a base, such as potassium hydroxide, or by acylation using a carboxylic acid chloride or anhydride in a non-hydroxylic solvent in the presence of a base such as trimethylamine, triethylamine or piperidine. The optional dehydration of the resulting compound of formula (I) wherein $R_5$ is hydroxy and $R_6$ is hydrogen, so as to obtain the corresponding compound of formula (I) wherein $R_5$ and $R_6$ together are a bond, may be carried out under conventional dehydration conditions, for example, by using a dehydrating agent, such as sodium hydride, in an inert solvent, such as dry tetrahydrofuran, at reflux temperature.

The optional reduction of the resulting compound of formula (I) wherein $R_5$ and $R_6$ together are a bond, so as to obtain the corresponding compound of formula (I) wherein $R_5$ and $R_6$ are both hydrogen, may be carried out in conventional manner by catalytic hydrogenation using palladium on charcoal.

The optional formation of a pharmaceutically acceptable salt, when one or the other of $R_1$ and $R_2$ in the resulting compound of formula (I) is amino or an amino-containing group, may be carried out conventionally.

Compounds of formula (II) may be prepared by the reaction of a compound of formula (VI):

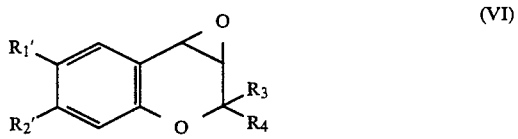

wherein $R_1'$, $R_2'$, $R_3$ and $R_4$ are as hereinbefore defined with a compound of formula (VII) or an acid addition salt thereof; with a compound of formula (VII):

$$H_2NCH_2CO_2R_8 \quad (VII)$$

wherein $R_8$ is as hereinbefore defined.

The reaction preferably takes place under basic conditions to facilitate nucleophilic displacement; a favourable reaction medium is therefore sodium hydroxide in ethanol. The reaction takes place at elevated temperatures, preferably at reflux temperatures.

The compounds of formula (VI) are known compounds and can be prepared in accordance with the processes described in the aforementioned U.S. patents and European Patent Publications.

Compounds of the formulae (III), (IV), (V) and (VII) are known or are prepared conventionally.

The compounds of formula (II) are novel and form an aspect of the present invention.

It is preferred that the compounds of formula (I) are isolated in substantially pure form.

As mentioned previously, the compounds of formula (I) have been found to have blood-pressure lowering activity. They are therefore useful in the treatment of hypertension. They are also of potential use in the treatment of other disorders hereinbefore referred to.

The present invention accordingly provides a pharmaceutical composition which comprises a compound of formula (I) or a pharmaceutically acceptable salt thereof and a pharmaceutically acceptable carrier. In particular, the present invention provides an anti-hypertensive pharmaceutical composition which comprises an anti-hypertensive effective amount of a compound of formula (I) or a pharmaceutically acceptable salt thereof and a pharmaceutically acceptable carrier.

The compositions are preferably adapted for oral administration. However, they may be adapted for other modes of administration, for example parenteral administration for patients suffering from heart failure. Other alternative modes of administration include sublingual or transdermal administration.

In order to obtain consistency of administration it is preferred that a composition of the invention is in the form of a unit-dose. Suitable unit dose forms include tablets, capsules and powders in sachets or vials. Such unit dose forms may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 1 to 200 mg for a 70 kg human adult and more particularly fom 1 to 10 mg.

With the above indicated dosage range, no adverse toxicological effects are indicated with the compounds of the invention.

The compositions of the invention may be formulated with conventional excipients, such as a filler, a disintegrating agent, a binder, a lubricant, a flavouring agent. They are formulated in conventional manner, for example in a manner similar to that used for known anti-hypertensive agents, diuretics and β-blocking agents.

It is greatly preferred that the compound of formula (I) or a pharmaceutically acceptable salt thereof is administered in the form of a unit-dose composition, such as a unit dose oral or parenteral composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate.

Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

In addition such compositions may contain further active agents such as anti-hypertensive agents and diuretics.

As is comnon practice, the compositions will usually be accompanied by written or printed directions for use in the medical treatment concerned.

The present invention further provides a compound of the formula (I) or a pharmaceutically acceptable salt thereof for use as an active therapeutic substance, in particular in the treatment of hypertension.

The present invention yet further provides a method of treating hypertension in mammals including man, which comprises administering to the suffering mammal an anti-hypertensive effective amount of a compound of formula (I) or a pharmaceutically acceptable salt thereof or a pharmaceutical composition of the invention.

The following examples relate to the preparation of compounds of formula (I); and the following descriptions to intermediates thereto.

DESCRIPTION 1

Trans 6-cyano-3,4-dihydro-2,2-dimethyl-4-(N-carbethoxymethyleneamino)-2H-benzo[b]pyran-3-ol (D1)

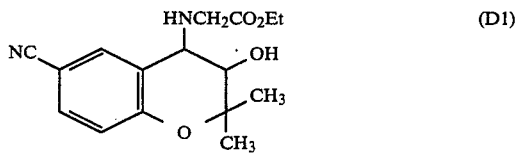

A mixture of 6-cyano-3,4-dihydro-2,2-dimethyl-3,4-epoxy-2H-benzo[b]pyran (5.0 g, the preparation of which was described in U.K. patent No. 1,511,187), glycine ethyl ester hydrochloride (2.59 g) and sodium hydroxide (0.75 g) in ethanol (100 mls) was refluxed for 7h. Filtration, evaporation, and chromatography gave the title compound (1.5 g). Recrystaisation of a small portion from ethyl acetate-pentane gave crystals of m.p. 98°–100° C.

NMR (CDCl$_2$-D$_2$O)δ6 1.23 (3H, s), 1.29 (3H, t, J=7 Hz), 1.52 (3H, s), 3.38 (1H, d, J=10 Hz) overlapping, 3.40–3.50 (2H, narrow m), 3.77 (1H, d, J=10 Hz), 4.23 (2H, q, J=7 Hz), 6.84 (1H, s, J=8 Hz), 7.43 (1H, q, J=8, 2 Hz), 7.75–7.85 (1H, narrow m).

DESCRIPTION 2

Trans-4-[N-(carbethoxymethyl)-N-(1-oxo-2-carbethoxyethyl)]amino-6-cyano-3,4-dihydro-2,2-dimethyl-2H-benzo b]pyran-3-ol (D2)

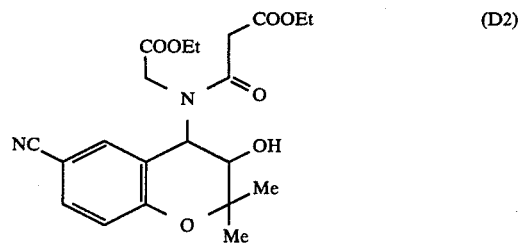

Ethyl malonyl chloride (0.85 ml) was added to a stirred solution of trans-6-cyano-3,4-dihydro-2,2-dimethyl-4-(N-carbethoxymethyleneamino)-2H-benzo[b]pyran-3-ol (2.0 g) and triethylamine (0.90 ml) in methylene chloride (50 ml) at 0° C. After 0.5 h the reaction mixture was allowed to attain room temperature. Water was added and the two layers separated. The organic layer was washed with dilute HCl (1N), water and brine and dried over anh. MgSO$_4$. Filtration and evaporation gave a crude product (2.20 g) which was chromatographed on silica gel using a gradient elution technique with 10–50% ethyl acetate-pentane. Fractions containing the desired compound were collected (1.44 g).

Mass spectrum (EI): MH$^+$ at 419.1818. C$_{21}$H$_{27}$N$_2$O$_7$ requires m/z 419.1818. M$^+$-H$_2$O$^+$ at 400.1640. C$_{21}$H$_{24}$N$_2$O$_6$ requires m/z 400.1634.

EXAMPLE 1

Trans-6cyano-3,4-dihydro-2,2-dimethyl-4-(3-methtl-2-4-dioxo-1-imidazolidinyl)-2H-benzo[b]pyran-3-ol (EI)

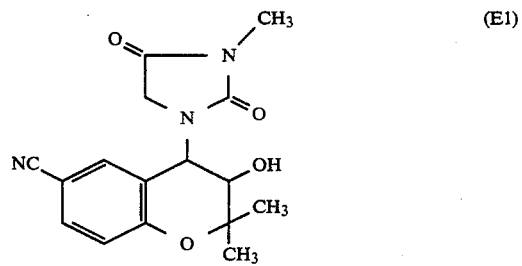

To a solution of methyl isocyanate (0.097 mls) in dichloromethane (20 mls) at 5° C. was added dropwise a solution of trans-cyano-3,4-dihydro-2,2-dimethyl-4-(N-carbethoxymethyleneamino)-2H-benzo[b]pyran-3-ol (0.5 g) in dichloromethane (20mls). After stirring for ½ h the reaction was warmed to room temperature and stirred for 16 h Evaporation and chromatography (chromatotron, pentane-ethylacetate gradient elution, mm silica gel) gave a fraction (220 mgs) which was recrystallised from ethyl acetate-pentane to give the title compound (120 mgs) of m.p. 257.5°–258.5° C.

NMR (CDCl$_3$/CD$_3$OD)δ1.31 (3H, s) 1 55 (3H, s), 3.13 (3H, s), 3.55 (1H, d, J=17 Hz) overlapping, 3.68 (1H, d, J=11 Hz), 3.90 (1H, d, J=17 Hz), 5 20 (1H, d, J=11 Hz), 6.92 (1H, d, J=8 Hz), 7.36 (1H, narrow m), 7.50 (1H, q, J=8, 2 Hz).

EXAMPLE 2

Trans-6-cyano-3,4-dihydro 4-N-(2,4-dioxo-1-pyrrolidinyl)-2,2-dimethyl-2H-benzo[b]pyran-3-ol (E2)

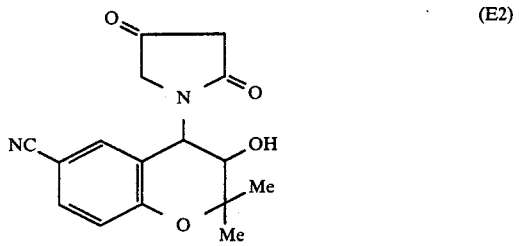

The compound of description 2 (6.30 g) and sodium ethoxide (2.10 g) in ethanol (200 ml) were stirred under nitrogen for 2 h. Water (100 ml) was added and the ethanol evaporated. The aqueous phase was acidified with dilute HCl and extracted with chloroform to give a foam (4.47 g) which was refluxed for 8 h in a mixture of acetonitrile (60 ml) and water (2 ml). Evaporation gave a solid (3.90 g) a portion of which was recrystallised from tetrahydrofuran-pentane to give the title compound (0.30 g) mp 310° C.

Mass spectrum M$^+$-H$_2$O at 282.1008. C$_{16}$H$_{14}$N$_2$O$_3$ requires m/z 282.1004.

EXAMPLE 3

Trans-6-Cyano-3,4-dihydro-2,2-dimethyl-4-(2,5-dioxo-1-piperazinyl)-2H-benzo[b]pyran-3-ol (E3)

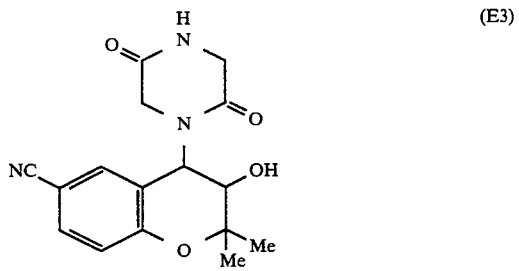

To a solution of N-carbobenzoxy-glycine (1.44 g) and hydroxybenzotriazole (2.10 g) in dry dimethylformamide (15 ml) at 0° C. under nitrogen was added dicyclohexylcarbodiimide (1.36 g). After 1 h the reaction mixture was allowed to attain room temperature for a further 1 h before recooling to 0° C. Trans-6-cyano-3,4-dihydro-2,2-dimethyl-4-(N-carbethoxymethyleneamino)-2H-benzo[b]pyran-3-ol (1.0 g) was added to the solution which was stirred for a further 2 h at 0° C., and 12 h at ambient temperature.

The solution was evaporated and the residue taken up in ethyl acetate, and filtered. The filtrate was washed with dil HCl, water, saturated aqueous NaHCO$_3$ solution water and brine before drying over anh. MgSO$_4$. Removal of drying agent and evaporation gave a residue (1.40 g) which was shaken with 10% Pd/C in an atmosphere of hydrogen, and then chromatographed (chromatotron—CHCl$_3$ to CHCl$_3$/20% MeOH gradient elution—2 mm silica gel). Fractions containing the desired product were combined and recrystallised twice to give the title compound (45 mg) as needles from EtOH, mp 292°–295° C. (d).

NMR (DMSOd$_6$ +D$_2$O)δ1.33 (3H,s), 1.58 (3H,s), 3.14–4.53 (5H, series of m), 5.68 (1H,d,J=10 Hz), 7.10 (1H,d,J=9 Hz), 7.50–7.85 (2H,m), Mass Spectrum: M$^+$-H$_2$O at m/z 297.

EXAMPLE 4

6-Cyano-2,2-dimethyl-4-(3-methyl-2,4-dioxo-1-imidazolidinyl)-2H-benzo[b]pyran (E4)

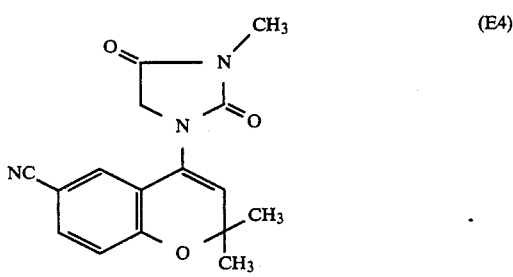

To the compound of example 1 (0.51 g) in tetrahydrofuran (40 mL) was added NaH (47 mg, 80% dispersion in oil), and the mixture heated under reflux for 3 h. After cooling, the mixture was poured into H$_2$O, and the mixture acidified with citric acid. Extraction via EtOAc gave a solid (380 mg) which was recrystallised from EtOAc-pentane to give the title compound (185 mg); mp 188°–190° C.

Mass Spectrum (EI) M$^+$ at m/z 297.1118. Calcd for C$_{16}$H$_{15}$N$_3$O$_3$: 297.113.

PHARMACOLOGICAL DATA

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005, was used to display pulses Prior to all measurements rats were placed in a heated environment (33.5°±0.5° C.) before transfer to a restraining cage. Each determination of blood pressure was the mean of at least 6 readings. Spontaneously hypertensive rats (ages 12–18 weeks) with systolic blood pressures ≦170 mmHg were considered hydertensive.

| Compound of Example 1 | Time Post Dose Hours | % Change in Systolic Blood Blood | % Change in Heart Rate |
|---|---|---|---|
| 5 rats Dose 1 mg/kg p.o. | 1* | −22 | −2 |
| | 2** | −41 ± 4 | −3 ± 3 |
| Initial Blood Pressure | 4** | −26 ± 4 | −7 ± 5 |
| 198 ± 3 mmHg | 6** | −42 ± 4 | −14 ± 4 |
| Initial Heart Rate 511 ± 12 beats/min | 24 | 2 ± 3 | −7 ± 3 |

*2 rats had no measurable pulse
**1 rat had no measurable pulse
Other compounds of the Examples were also tested and found to be active.

Toxicity

No toxic effects were observed in the above tests.

I claim:
1. A compound of formula (I):

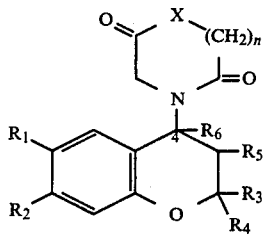

either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or amino-sulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino, $C_{1-6}$, alkoxysulpinylamino, or $C_{1-6}$, alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;

one of $R_3$ and $R_4$ is hydrogen or $C_{1-4}$ alkyl and the other is $C_{1-4}$ alkyl or $R_3$ and $R_4$ together are $C_{2-5}$ polymethylene;

either $R_5$ is hydrogen, hydroxy, $C_{1-6}$ alkoxy or $C_{1-7}$ carboxylic acyloxy and $R_6$ is hydrogen or $R_5$ and $R_6$ together are a bond;

n is 0 or 1; and

X is $CH_2$ or $NR_7$ wherein $R_7$ is hydrogen or $C_{1-6}$ alkyl;

the nitrogen-containing group in the 4-position being trans to the $R_5$ group when $R_5$ is hydroxy, $C_{1-6}$ alkoxy or $C_{1-7}$ carboxylic acyloxy; or a pharmaceutically acceptable salt or solvate thereof.

2. A compound according to claim 1 wherein X is $CH_2$ and n is 0.

3. A compound according to claim 1 wherein one of $R_1$ and $R_2$ is hydrogen and the other is selected from the class of $C_{1-6}$ alkylcarbonyl, $C_{1-6}$ alkoxycarbonyl, nitro or cyano.

4. A compound according to claim 3 wherein $R_1$ is acetyl, nitro or cyano and $R_2$ is hydrogen.

5. A compound according to claim 1 wherein $R_3$ and $R_4$ are both methyl groups.

6. A compound according to claim 1 wherein $R_5$ is hydroxy and $R_6$ is hydrogen.

7. A compound according to claim 1 wherein n is 0 or 1 and X is $NR_7$ wherein $R_7$ is as defined in claim 1.

8. A compound according to claim 8 wherein $R_7$ is methyl.

9. A compound selected from the group consisting of: trans-6-cyano-3,4-dihydro-2,2-dimethyl-4-(3-methyl-2-4-dioxo-1-imidazolidinyl)-2H-benzo[]pyran-3-ol, trans-6-cyano-3,4-dihydro-4-N-(2,4-dioxo-1-pyrrolidinyl)-2,2-dimethyl-2H-benzopyran-3-ol, trans-6-cyano-3,4-dihydro-2,2-dimethyl-4-(2,5-dioxo-1-piperazinyl)-2H-benzopyran-3-ol and 6-cyano-2, 2dimethyl-4-(3-methyl-2,4-dioxide-1-imidazalidinyl)pyran.

10. Trans-6-cyano-3,4-dihydro-2,2-dimethyl-4-(2,5-dioxo-1-piperazinyl)-2H-benzopyran-3-ol.

11. An anti-hypertensive pharmaceutical composition comprising an effective amount of a compound according to claim 1 or a pharmaceutically acceptable salt thereof and a pharmaceutically acceptable carrier.

12. A method of treatment of hypertension in mammals which comprises the administration to the mammal of an effective amount of a compound according to claim 1 or a pharmaceutically acceptable salt thereof.

* * * * *